United States Patent [19]

Sterzer

[11] Patent Number: 5,007,437
[45] Date of Patent: Apr. 16, 1991

[54] CATHETERS FOR TREATING PROSTATE DISEASE

[75] Inventor: Fred Sterzer, Princeton, N.J.

[73] Assignee: MMTC, Inc., Princeton, N.J.

[21] Appl. No.: 512,520

[22] Filed: Apr. 19, 1990

Related U.S. Application Data

[63] Continuation of Ser. No. 367,718, Jun. 16, 1989, abandoned.

[51] Int. Cl.$^5$ .............................................. A61N 5/02
[52] U.S. Cl. ..................... 428/786; 128/788; 128/804; 128/401
[58] Field of Search ............... 128/784, 786, 788, 804, 128/401

[56] References Cited

U.S. PATENT DOCUMENTS

| | | | |
|---|---|---|---|
| 4,311,154 | 1/1982 | Sterzer et al. | 128/804 |
| 4,601,296 | 7/1986 | Yerushelmi | 128/804 |
| 4,662,383 | 5/1987 | Sogawa et al. | 128/784 |
| 4,676,258 | 6/1987 | Inokochi et al. | 128/804 |
| 4,823,812 | 4/1989 | Eshel et al. | 128/804 |

Primary Examiner—Lee S. Cohen
Attorney, Agent, or Firm—George Seligsohn

[57] ABSTRACT

Applying squeezing pressure to a diseased prostate, by means of a urethral and/or rectal catheter incorporating an inflatable prostate balloon, to compress the prostate while it is being irradiated from a microwave antenna, increases the therapeutic temperature to which the prostate tissue more distal to the microwave antenna can be heated without heating any non-prostate tissue beyond a maximum safe temperature, and reduces the temperature differential between the heated more distal and more proximate prostate tissue from the microwave antenna.

15 Claims, 4 Drawing Sheets

CATHETERS FOR TREATING PROSTATE DISEASE

This is a continuation of application Ser. No. 07/367,718, filed Jun. 16, 1989, now abandoned.

BACKGROUND OF THE INVENTION

This invention relates to the use of microwaves for the treatment of prostate disease and, more particularly, to catheters designed to efficiently irradiate the prostate of a male patient with microwave power.

As known in the art, prostate disease, such as prostate cancer or benign prostatic hypertrophy (BPH), inter alia, results in a narrowing of the urethra in the neighborhood of the prostate caused by the surrounding enlarged prostate. This narrowing restricts the passage of urine. As is also known, a diseased prostate can be treated by irradiating prostate tissue with an amount of microwave power sufficient to heat that prostate tissue to a therapeutic temperature. However, the maximum microwave power that can be used is limited by the fact that it is essential that none of the prostate tissue be overheated beyond a maximum therapeutic temperature and that none of the irradiated non-prostate tissue be heated beyond a maximum safe temperature (which maximum safe temperature for non-prostate tissue is below the maximum therapeutic temperature for prostate tissue).

Catheters designed to be inserted into the urethra that help pass urine and bulb applicators designed to be inserted into the rectum of the patient, which have been fitted with a microwave antenna, have been used in the past to irradiate the prostate tissue of the patient with microwave power. A urethral catheter is often equipped with a so-called Foley balloon located close to the tip thereof, which may be inflated (usually with air) after the tip of the urethral catheter has been inserted into the patient's bladder, thereby to secure the catheter at its fully inserted position within the patient's urethra. A bulb applicator may be made non-symmetrical so that, after full insertion into a patient's rectum, the microwave power preferentially irradiates the patient's prostate tissue.

Regardless of whether the patient's prostate tissue is irradiated with microwave power radiated by the microwave antenna from the patient's urethra or rectum, it is apparent that non-prostate tissue situated between the patient's prostate and urethra or rectum, as the case may be, also will be irradiated. Further, since the microwave field intensity tends to vary as an inverse function (e.g., as an inverse square) of distance from the microwave antenna, this non-prostate tissue will be more highly irradiated than will the prostate tissue (particularly that prostate tissue situated more distal to the microwave antenna), because the irradiated non-prostate tissue is more proximate to the microwave antenna. Therefore, the difference between the respective microwave-field intensities heating the more proximate irradiated non-prostate tissue and the more distal irradiated prostate tissue varies as an inverse function of the ratio of their respective distances from the microwave antenna. Thus, in order to heat the more distal prostate tissue to a higher therapeutic temperature without concurrently either overheating any of the more proximate prostate tissue or heating the more proximate non-prostate tissue beyond a maximum safe temperature, it would be desirable to increase the minimum distance between the microwave antenna and the more proximate non-prostate tissue, without appreciably affecting the distance between the more distal prostate tissue.

SUMMARY OF THE INVENTION

The present invention contemplates increasing the minimum distance between the microwave antenna and the more proximate non-prostate tissue by applying squeezing pressure to such more proximate tissue.

More specifically, the present invention is directed to an improved catheter adapted to be inserted into an orifice of a male patient for treating prostate disease, wherein the catheter comprises means including microwave antenna means for irradiating the patient's prostate with a given distribution of microwave field intensity, thereby to heat tissue of the patient to a temperature which tends to vary as a direct function of microwave power and as an inverse function of the distance of that tissue to the microwave antenna means, and wherein the maximum microwave power to be employed is limited to an amount at which the temperature of the patient's heated tissue most proximate to the microwave antenna means does not exceed a given safe maximum temperature.

The improvement comprises an inflatable balloon (1) which is adapted to be in a deflated state while the catheter is being inserted into the orifice, (2) which is located in the catheter at a position which is in cooperative relationship with the patient's prostate when the catheter is fully inserted, and (3) which is adapted to be inflated when the catheter is fully inserted for applying squeezing pressure to both prostate tissue and that non-prostate tissue situated between the inflated balloon and the prostate tissue, thereby increasing the minimum distance between heated tissue of the patient and the microwave antenna means. The desirable result is that the maximum microwave power may be increased without exceeding the given maximum safe temperature and the temperature differential between the heated prostate tissue more proximate to the microwave antenna means and the heated prostate tissue more distal to the one microwave antenna means is reduced.

PREFERRED EMBODIMENTS OF THE INVENTION

Figure 1:
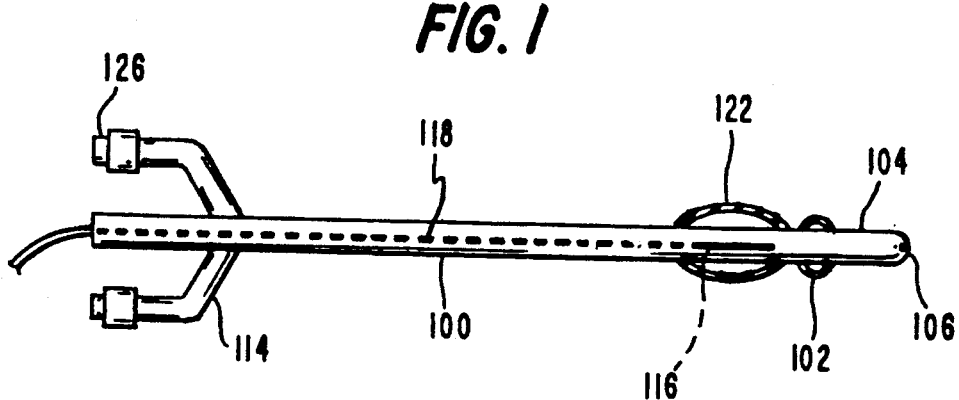
FIGS. 1, 1a and 1b, taken together, diagrammatically illustrate a urethral catheter for treating prostate disease, which urethral catheter incorporates a first embodiment of the present invention.
Figure 1B:
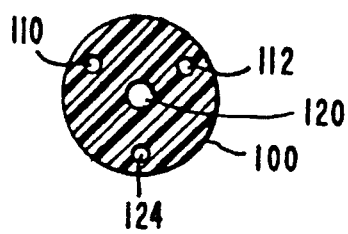
Figure 1A:
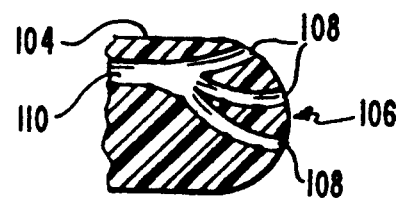

Like urethral catheters of the prior art, the urethral catheter shown in FIGS. 1, 1a and 1b comprises a member defining longitudinal catheter bore 100 and an inflatable Foley balloon 102 surrounding bore 100. A tip portion 104, located in front of Foley balloon 102, terminates bore 100 in a smooth tip 106. Tip portion 104 together with Foley balloon 102 in a deflated state are intended to be inserted into the bladder of a patient and then, by inflation of Foley balloon 102, catheter bore 100 is maintained in substantially fixed position within the urethra of the patient. As indicated in FIG. 1a, tip 106 includes several perforations 108 which permit urine to be channeled from the patient's bladder to urine lumen 110 of bore 100, through which the patient discharges urine. In order to inflate Foley balloon 102, lumen 112 (FIG. 1b) extends from Foley balloon 102 to Foley balloon inflation valve 114 attached to the rear of bore 100. Treatment of prostate disease with microwaves requires that the urethral catheter includes a properly-located microwave antenna 116, which is connected to an external microwave power source over transmission line 118 (FIG. 1) that runs through microwave lumen 120 (FIG. 1b). Further, as known but omitted from the drawing, treatment of prostate disease with microwaves requires the use of a thermometer (preferably digital), including one or more suitably-placed temperature sensing probes, for ascertaining the temperature of tissue heated by the microwaves.

In accordance with the principles of the present invention, the urethral catheter shown in FIGS. 1, 1a and 1b also includes prostate balloon 122 surrounding bore 100 and longitudinally located behind Foley balloon 102 and in cooperative relationship with microwave antenna 116. More specifically, microwave antenna 116 and prostate balloon 122 are longitudinally situated at a distance from tip 106 such that when bore 100 is fully inserted in the urethra of a patient, elements 116 and 122 are in cooperative alignment with the patient's prostate. In order to inflate prostate balloon 122, prostate balloon lumen 124 (FIG. 1b) extends from prostate balloon 122 to one or more prostate balloon inflation valves 126 attached to the rear of bore 100. Preferably, microwave antenna 116 and microwave lumen 120 are axially situated with respect to the axis of bore 100 (in which case the other lumens 110, 112 and 124 are situated off-axis, as shown in FIG. 1b), so that the distribution of the microwave field intensity irradiating the patient's prostate is angularly non-directional.

The size of catheters is conventionally measured in FRENCH units, A typical size for the urethral catheter shown in FIG. 1 is 16 FRENCH. Typically, the length of bore 100 between its tip and its attachment to valves 114 and 126 is about 360 millimeters (mm); the length of tip portion 104 is about 25 mm; the length of Foley balloon 102 is about 10 mm; the distance between Foley balloon 102 and prostate balloon 122 is about 4 mm; and the length of prostate balloon 122 is about 40 mm. Further, the minimum diameter of microwave lumen 120 is about 2.5 mm.

In practice, while the catheter shown in FIGS. 1, 1a and 1b is being inserted into the urethra of a patient with prostate disease, both the Foley and prostate balloons are in a deflated state. This both makes for easier insertion and minimizes pain to the patient. After full insertion (i.e., the deflated Foley balloon reaching into the patient's bladder), a fluid (usually air) is pumped through the Foley inflation valve thereby to inflate the Foley balloon and hold the catheter within the patient's urethra. However, the catheter is still capable of limited longitudinal movement with respect to the urethra. After the Foley balloon has been inflated, a fluid, preferably a low-loss radio-opaque liquid (e.g., deionized water in which a small amount of a radio-opaque substance has been dissolved), is slowly pumped through the one or more prostate inflation valves into the prostate balloon. The use of a radio-opaque liquid permits fluoroscopy of inflated prostate balloon 206-b to be employed to first align the longitudinal position of the prostate balloon with the patient's prostate and then insure that the prostate balloon is inflated by the proper amount to apply a squeezing pressure that results in a desired compression of the prostate tissue.

It is desired to heat the diseased prostate tissue to a therapeutic temperature without heating the non-prostate tissue lining the urethra, which intervenes between the microwave antenna and this prostate tissue, beyond a maximum safe temperature. However, the irradiating microwave field intensity, which varies as an inverse function (e.g., inverse square) of the distance between the microwave antenna and the heated tissue, is higher for the intervening non-prostate tissue than it is for the prostate tissue and is higher for the more proximate prostate tissue than it is for the more distal prostate tissue. The use of an inflated prostate balloon, employed by the present invention, mitigates this problem, as shown in FIGS. 2a and 2b.

Figure 2A:
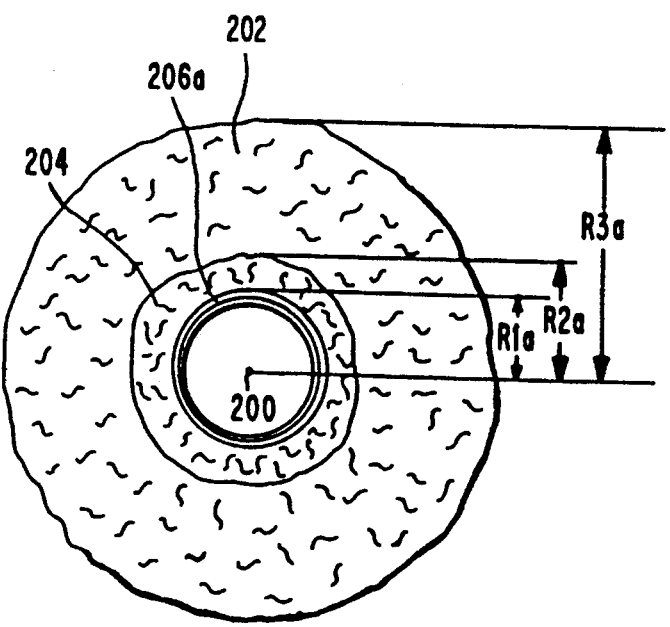
FIGS. 2a and 2b, taken together, illustrate the advantages of the aforesaid urethral catheter.
Figure 2B:
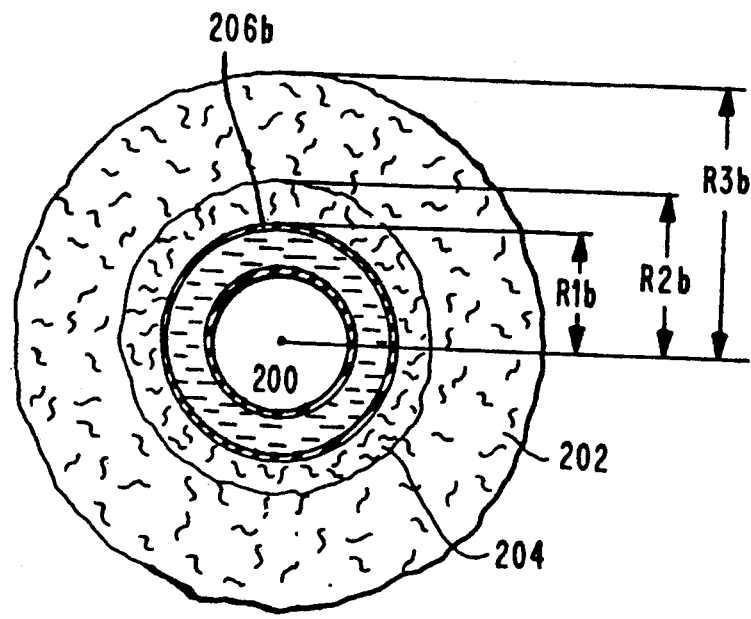

FIGS. 2a and 2b show that the radial distances of the urethral catheter from microwave antenna 200 to prostate tissue 202 and intervening non-prostate tissue 204 with a deflated prostate balloon 206-a and with an inflated prostate balloon 206-b, respectively. As shown, inflated prostate balloon 206-b forms a circuferentially symmetrical toroid extending around the entire circumference of the urethral catheter. Specifically, the radial distance $R_{1b}$ from microwave antenna 200 to the beginning of non-prostate tissue 204 with inflated prostate balloon 206-b is significantly larger than the corresponding radial distance $R_{1a}$ with deflated prostate balloon 206-a. Similarly, the inner radius $R_{2b}$ of prostate tissue 202 with inflated prostate balloon 206-b is significantly larger than the corresponding radial distance $R_{2a}$ with deflated prostate balloon 206-a. However, of particular significance is that, because prostate tissue is soft and compressible, the difference between the outer and inner radii $R_{3b}$ and $R_{2b}$ of prostate tissue 202 with inflated prostate balloon 206-b is substantially reduced with respect to the corresponding difference between radii $R_{3a}$ and $R_{2a}$ with deflated prostate balloon 206-a. Thus, both the variation in the respective microwave field intensities heating any part of the intervening non-prostate tissue and heating any part of the diseased prostate tissue and the variation in the respective microwave field intensities heating the more proximate and more distal prostate tissue are significantly reduced by the use of an inflated prostate balloon. This makes it possible to heat the prostate tissue more evenly and to higher therapeutic temperatures without heating any part of the non-prostate tissue beyond its maximum safe temperature.

Figure 1C:
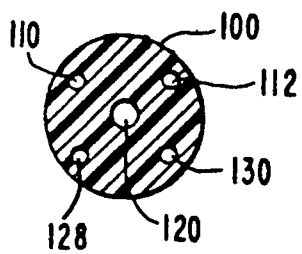
FIG. 1c diagrammatically illustrates a modification of the aforesaid urethral catheter.

Obviously, increasing the microwave power radiated from the microwave antenna will tend to increase the respective temperatures reached by both the prostate tissue and the intervening non-prostate tissue. The modification of the urethral catheter shown in FIG. 1c makes it possible to increase the microwave power, to thereby increase the therapeutic temperatures reached by the more distal parts of the diseased prostate tissue without overheating the more proximate parts of the prostate tissue or any part of the intervening non-prostate tissue lining the urethra. The modification comprises replacing single prostate balloon lumen 124 of FIG. 1b with both prostate balloon inlet lumen 128 and prostate balloon outlet lumen 130 of FIG. 1c. This permits the pumped fluid (e.g., radio-opaque liquid) inflating prostate balloon 122 to be circulated therethrough and act as a coolant for removing heat preferentially from the non-prostate tissue adjacent thereto. Either or both of inlet and outlet lumens 128 and 130 may be associated with a prostate balloon inflation valve 126, shown in FIG. 1, which may be operated by a thermostat that controls the circulation of the coolant in a manner to maintain the non-prostate tissue at a temperature near, but never exceeding, its maximum safe temperature.

Figure 3:
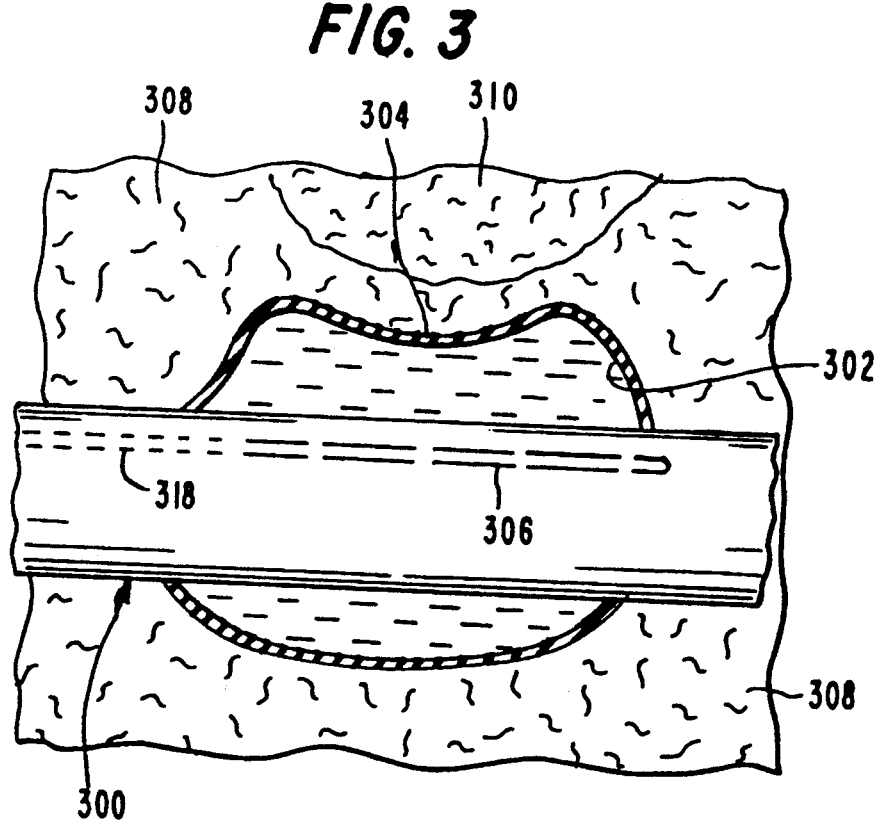
FIG. 3 diagrammatically illustrates a rectal catheter for treating prostate disease, which rectal catheter incorporates a second embodiment of the present invention, and also illustrates the advantages of this rectal catheter.

As is known, prostate disease is often treated with microwaves applied to the prostate tissue from the patient's rectum by means of a bulb applicator. A diseased prostate, which is enlarged, tends to form a bulge which protrudes into the patient's rectum. A problem with such a bulb applicator is that its insertion into the rectum tends to push aside the protruding bulge, which is quite painful to the patient. The rectal catheter shown in FIG. 3, which forms a second embodiment of the present invention, overcomes this problem. In addition, the rectal catheter shown in FIG. 3 also possesses the advantages of the urethral catheter, discussed above. More particularly, while the structure of the rectal catheter is generally similar to that of the urethral catheter discussed above (either with or without the modification shown in FIG. 1c), it differs therefrom in several ways. First, the rectal catheter has a larger diameter bore 300 in order to properly fit the rectum. Second, because an inflated balloon is elastic, prostate balloon 302, when inflated, forms a bowl 304 that stretches to substantially conform to the bulge of the enlarged prostate protruding into the patient's rectum (rather than being circumferentially symmetrical like the urethral catheter discussed above). Third, because the prostate is located only on one side of the rectum, microwave antenna 306 (energized through transmission line 318) is situated off axis, closer to the prostate, so that the prostate tissue and the intervening non-prostate tissue between the prostate and rectum is preferentially irradiated with respect to the irradiation of the remaining non-prostate tissue surrounding the rectum. A more complex antenna means incorporating a directional microwave antenna (which may be utilized to further preferentially irradiate the prostate tissue. Further, such a directional antenna need not necessarily be situated off axis in order to preferentially irradiate the prostate tissue.

Figure 3A:
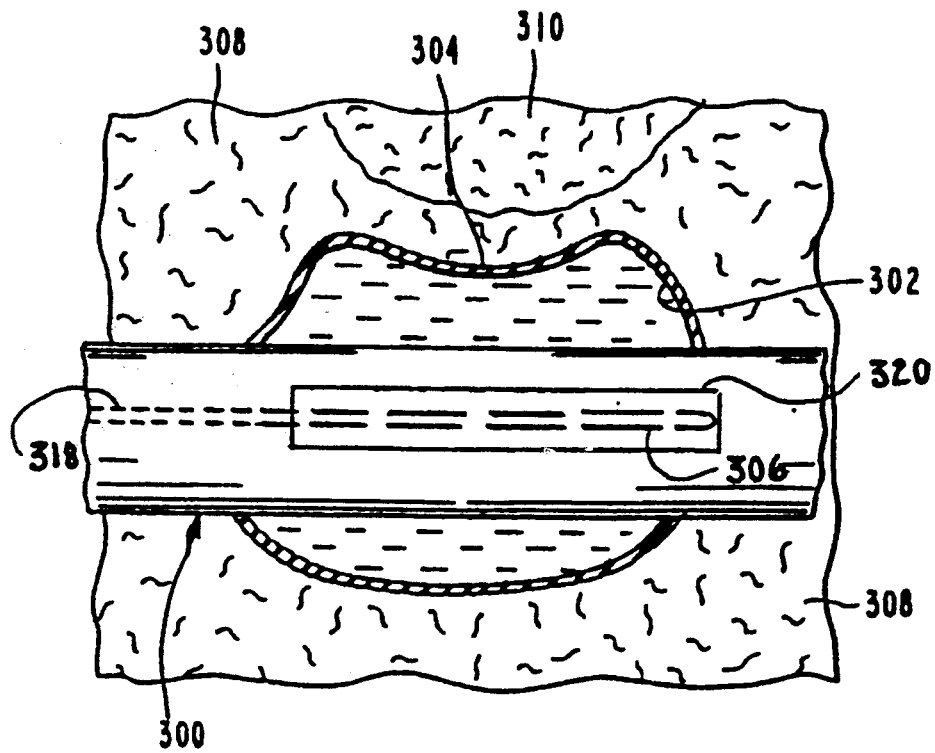
FIGS. 3a and 3b, taken together, illustrate a first modification of the rectal catheter illustrated in FIG. 3.
Figure 3B:
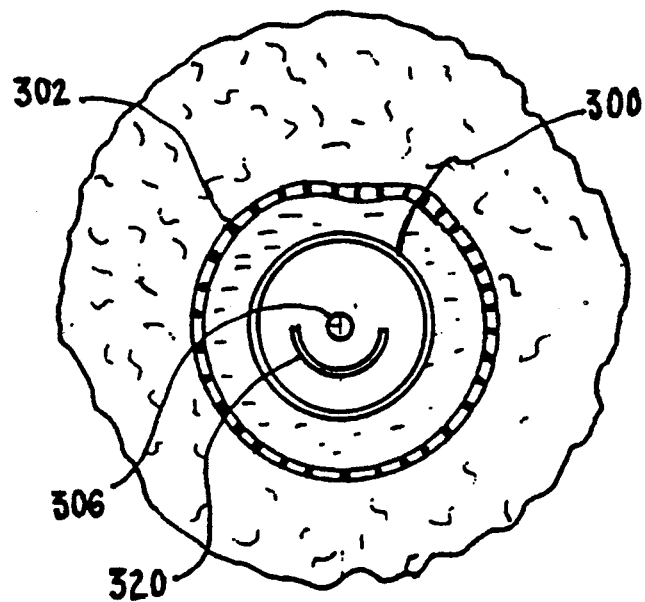

FIGS. 3a and 3b, taken together, shown an example of a rectal catheter employing a directional microwave antenna comprised of reflector 320 partially surrounding centrally-located microwave antenna 306 and positioned to preferentially irradiate the prostate tissue.

Figure 3C:
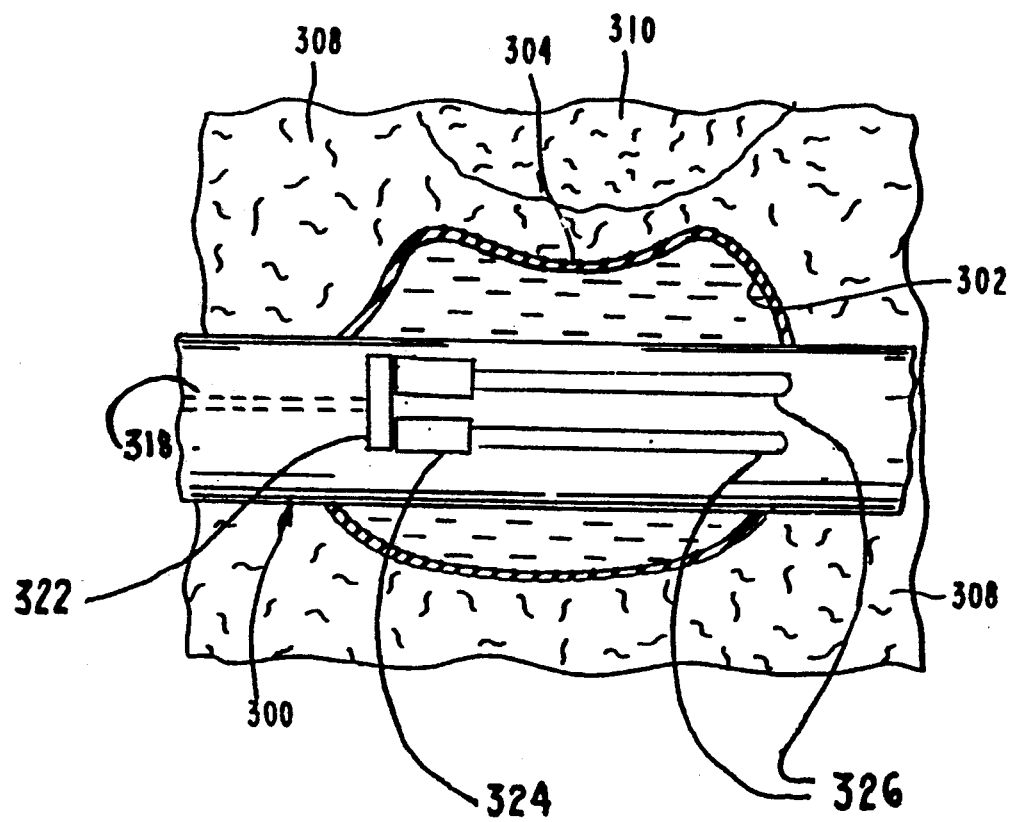
FIGS. 3c and 3d, taken together, illustrate a second modification of the rectal catheter illustrated in FIG. 3.
Figure 3D:
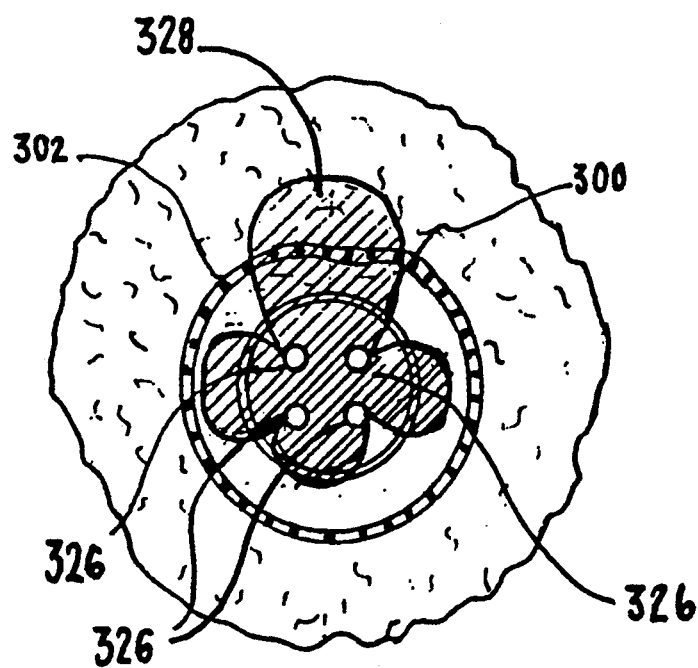

FIGS. 3c and 3d, taken together, show an example of a rectal catheter employing a directional microwave antenna comprised of a phased array made up of a power splitter 322, four phase shifters 324 and four antenna elements 326. Power splitter 322 distributes the microwave power applied through transmission line 318 to each of the four antenna elements 326 through one of the four phase shifters 324. Each of the four phase shifters is appropriately adjusted to cause the four antenna elements 326 to emit a shaped radiation pattern 328 that preferentially irradiates the prostate tissue.

In practice, the rectal catheter is inserted into the rectum of the patient with its prostate balloon 302 in a deflated state. This substantially eliminates the pain that the patient felt when a bulb applicator was inserted. Before inflating prostate balloon 302, it is oriented in substantial cooperative relationship with the bulge of prostate tissue and intervening non-prostate tissue. Therefore, slow inflation of prostate balloon 302 results in the creation of a bowl portion 304, which first conforms to the bulge, and then slowly compresses both the prostate tissue 310 and that non-prostate tissue 308 which intervenes between prostate tissue 310 and bowl portion 304 of inflated prostate balloon 302, to finally reach the state shown in FIG. 3, without any substantial discomfort to the patient.

Microwave power transmitted from two or more separated antennas may be used to simultaneously irradiate the diseased prostate of a patient. Thus, both the urethral and rectal catheters disclosed herein may be used at the same time to treat prostate disease. In fact, some or all of the irradiating microwave power may originate from outside of the patient's body, so long as squeezing pressure is then being applied to the prostate, preferably from the urethra, in accordance with the principles of this invention.

In addition to the advantages of the present invention discussed above, it is believed that the simultaneous application of both squeezing pressure and heat to an enlarged prostate cooperate synergistically to effect a significantly more lasting deformation (i.e., reduction in size) of the enlarged prostate for a prolonged period of time after the heat and pressure have been removed, than could be obtained by the use of either squeezing pressure or heat alone.

What is claimed is:

1. In a catheter adapted to be inserted into an orifice of a male patient for treating prostate disease, wherein said catheter comprises means including microwave antenna means for irradiating said patient's prostate with a given distribution of microwave field intensity, thereby to heat tissue of said patient to a temperature which tends to vary as a direct function of microwave power and as an inverse function of the distance of that tissue to said microwave antenna means, and wherein the maximum microwave power to be employed is limited to an amount at which the temperature of the patient's heated tissue most proximate to said microwave antenna means does not exceed a given safe maximum temperature; the improvement wherein said catheter further comprises:

an inflatable balloon inside of which said microwave antenna means is situated, said balloon being structured to have a cross-section which is expandable in size from a first value no larger than the cross-section of said orifice when said balloon is deflated to a second value substantially larger than the cross-section of said orifice when said balloon is inflated to a given pressure, said given pressure being sufficient to squeeze and compress tissue of said patient adjacent said balloon and permit the size of said balloon cross-section to be expanded to its second value;

whereby said catheter may be (1) inserted into said orifice while in a deflated state and positioned therein at a location at which both said balloon and said microwave antenna means are in cooperative relationship with said patient's prostate for effecting the irradiation of said patient's prostate with said given distribution of microwave field intensity when said catheter is fully inserted into said orifice, and (2) said balloon may be inflated to said given pressure when said catheter is fully inserted for expanding the size of its cross-section to said second value, resulting in both prostate tissue and that non-prostate tissue situated between said inflated balloon and said prostate tissue being squeezed and compressed so as thereby to increase the minimum distance between said microwave antenna means situated inside of said balloon and heated tissue of said patient; and means for inflating said balloon to said given pressure;

whereby the maximum microwave power may be increased without exceeding said given maximum safe temperature and the temperature differential between the heated prostate tissue more proximate to said microwave antenna means and the heated prostate tissue more distal to said microwave antenna means is reduced.

2. The catheter defined in claim 1, wherein said orifice is said patient's urethra; and wherein:

said catheter has a circumference about a central axis thereof;

said balloon, when inflated to said given pressure, forms a circumferentially symmetrical toroid that extends around the entire circumference of said catheter for applying substantially equal squeezing pressure to compress the surrounding prostate tissue, thereby effectively increasing the internal diameter of said prostate; and said microwave antenna means is located substantially on the central axis of said catheter for applying a substantially angularly-uniform distribution of microwave field intensity to said prostate tissue.

3. The catheter defined in claim 2, wherein:

said catheter further comprises a second inflatable balloon disposed at an end of said catheter which is in cooperative relationship with the patient's bladder when the catheter is fully inserted, for securing said catheter to said bladder when said second balloon is inflated, and a lumen having an opening at said end, which opening is situated within said patient's bladder when the catheter is fully inserted, for permitting urine to be transported from said patient's bladder through said lumen to the outside of said patient's body.

4. The catheter defined in claim 3, wherein:

said catheter further comprises means including a second lumen for circulating a coolant for removing heat generated by said microwave power, whereby the maximum microwave power may be increased to heat the prostate tissue more distal from said microwave antenna means to a higher temperature without concurrently exceeding said given safe maximum temperature for the patient's heated tissue most proximate to said microwave antenna means.

5. The catheter defined in claim 1, wherein said orifice is said patient's rectum; and wherein:

said means including said microwave antenna means comprises distribution means for providing a distribution of microwave field intensity that preferentially heats said patient's tissue in a direction towards said patient's prostate more than said patient's tissue in a direction away from said patient's prostate.

6. The catheter defined in claim 5, wherein:

said microwave antenna means is offset from the axis of said catheter in a direction adapted to be oriented toward said patient's prostate when said catheter is fully inserted in said patient's rectum.

7. The catheter defined in claim 5, wherein:

said microwave antenna means includes a reflector adapted to be oriented to provide said distribution of microwave field intensity when said catheter is fully inserted in said patient's rectum.

8. The catheter defined in claim 5, wherein:

said microwave antenna means includes a phased array adapted to provide said distribution of microwave field intensity when said catheter is fully inserted in said patient's rectum.

9. The catheter defined in claim 5, wherein:

said balloon has a given shape, said given shape being configured so that expansion of the cross-section of a fully-inserted balloon from said first to said second values thereof results in said balloon first substantially conforming to a bulge in the patient's rectum caused by an enlarged prostate and then applying substantially equal squeezing pressure to said bulge for compressing said enlarged prostate.

10. The catheter defined in claim 5, wherein:

said catheter further comprises means including a second lumen for circulating a coolant for removing heat generated by said microwave power, whereby the maximum microwave power may be increased to heat the prostate tissue more distal from said microwave antenna means to a higher temperature without concurrently exceeding said given safe maximum temperature for the patient's heated tissue most proximate to said microwave antenna means.

11. The catheter defined in claim 1, wherein:

said means for inflating said balloon comprises means for inflating said balloon with a radio-opaque liquid, whereby the position of said balloon with respect to said patient's prostate can be monitored when said catheter is inserted in said patient's orifice.

12. A method for treating prostate disease of a patient; said method comprising the steps of:

applying sufficient squeezing pressure to non-prostate tissue which surrounds an orifice of the patient in the vicinity of the patient's prostate both to compress the prostate and non-prostate tissue and to increase the distance from a given location within said orifice to said non-prostate tissue; and while said pressure is being applied, irradiating said prostate through said non-prostate tissue from said given location within said orifice with microwave power sufficient to heat that prostate tissue which is more distal to said orifice to a first therapeutic temperature without heating any non-prostate tissue of the patient above a maximum safe temperature.

13. The method defined in claim 12, wherein:

the step of applying squeezing pressure comprises applying squeezing pressure to that non-prostate tissue which surrounds the patient's urethra thereby to increase the diameter of said urethra; and the step of irradiating said prostate includes the step of irradiating said prostate from said urethra.

14. The method defined in claim 13, further comprising the step of:

while said pressure is being applied to said tissue surrounding said patient's urethra and said prostate is being irradiated with microwave power from said patient's urethra, irradiating said patient's prostate from a position outside of said patient's urethra through second non-prostate tissue that is situated between said outside position and said prostate tissue with additional microwave power, said additional microwave power being sufficient to heat that prostate tissue which is more distal to said urethra and is situated between said patient's urethra and said second non-prostate tissue to a second therapeutic temperature that is higher than said first therapeutic temperature without heating said second non-prostate tissue above a maximum safe temperature.

15. The method defined in claim 13, further comprising the steps of:
while said pressure is being applied to said tissue surrounding said patient's urethra, applying additional squeezing pressure to tissue of the patient's rectum in the vicinity of the patient's prostate; and
while said prostate is being irradiated with microwave power from said patient's urethra, irradiating said patient's prostate from said patient's rectum with additional microwave power sufficient to heat that prostate tissue which is more distal to said urethra and is situated between said patient's urethra and rectum to a second therapeutic temperature that is higher than said first therapeutic temperature without heating non-prostate tissue proximate to said patient's rectum above a maximum safe temperature.

* * * * *